(12) United States Patent
Baginski et al.

(10) Patent No.: US 8,198,063 B1
(45) Date of Patent: Jun. 12, 2012

(54) RAPID DEGLYCOSYLATION OF GLYCOPROTEINS

(75) Inventors: Tomasz Baginski, Mountain View, CA (US); Thomas G. Warner, San Carlos, CA (US)

(73) Assignee: Pro Zyme, Inc, Hayward, CA (US)

( * ) Notice: Subject to any disclaimer, the term of this patent is extended or adjusted under 35 U.S.C. 154(b) by 843 days.

(21) Appl. No.: 11/854,516

(22) Filed: Sep. 12, 2007

Related U.S. Application Data (60) Provisional application No. 60/844,308, filed on Sep. 12, 2006.

(51) Int. Cl.
*C12N 9/24* (2006.01)
*C40B 50/06* (2006.01)

(52) U.S. Cl. .......................................... 435/200; 506/26

(58) Field of Classification Search .................. 435/200; 506/26
See application file for complete search history.

(56) References Cited

U.S. PATENT DOCUMENTS

| | | | |
|---|---|---|---|
| 4,925,796 A * | 5/1990 | Bergh et al. ...................... | 435/97 |
| 2002/0137068 A1* | 9/2002 | Haugland et al. .................. | 435/6 |
| 2004/0259142 A1* | 12/2004 | Chai et al. ......................... | 435/6 |
| 2006/0191026 A1 | 8/2006 | Zhu | |

OTHER PUBLICATIONS

Damon I. Papac, John B.Briggs, Edward T.Chin and Andrew J.S. Jones "A high-throughput microscale method to release N-linked oligosaccharides from glycoproteins for matrix-assisted laser desorption/ionization time-of-flight mass spectrometric analysis" Glycobiology vol. 8 No. 5 pp. 445-454, 1998.*
Qiagen "Product Profile: 96-Well-Plate Centrifugation System" 1009706 Aug. 1998 2 pgs.*
Anderson et al., "Monosaccharide and oligosaccharide analysis of isoelectric focusing-separated and blotted granulocyte . . . ", Glycobiology 4(4):459-467 (1994).
Bartles et al., "Biochemical Characterization of Domain-specific Glycoproteins of the Rat Hepatocyte Plasma Membrane", J Biol Chem 260(23):12792-12802 (1985).
Martin and Eliason, "Glycopeptidase F Treatment and Amino Acid Sequence . . . ", in Villafranca, ed. Techniques in Protein Chemistry II, Academic Press, San Diego, 1991.
Weitzhandler et al., "Monosaccharide and Oligosaccharide Analysis of Proteins Transferred to Polyvinylidence Fluoride Membranes . . . ", J Biol Chem 268(7):5121-5130 (1993).
Weitzhandler et al., "Analysis of Carbohydrates on IgG Preparations", J Pharmaceutical Sci, 83(12):1670-1675, (1994).

* cited by examiner

*Primary Examiner* — Jon P Weber
*Assistant Examiner* — Thane Underdahl
(74) *Attorney, Agent, or Firm* — Lawrence J. Hyman; Hyman IP Law (57) ABSTRACT

The present invention provides methods for rapid deglycosylation of glycoproteins.

17 Claims, 4 Drawing Sheets

RAPID DEGLYCOSYLATION OF GLYCOPROTEINS

CROSS-REFERENCES TO RELATED APPLICATIONS

This application claims the benefit of U.S. Provisional Application No. 60/844,308, filed Sep. 12, 2006, the contents of which are hereby incorporated by reference.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Many proteins are glycosylated, that is, they are conjugated to carbohydrates, forming a conjugate known as a glycoprotein. Often, the carbohydrates are oligomers that consist of several monosaccharide residues, which form a oligosaccharide, or glycan. These polymers can form straight or branched chains. When the carbohydrate is conjugated to the protein through a nitrogen atom, typically of an asparagine residue, the carbohydrate is referred to as an N-glycan.

Glycosylation is a post-translational modification of the protein, so it occurs after the protein is translated from its encoding nucleic acid. Since the carbohydrates conjugated to a protein can affect pharmacokinetics, stability, bioactivity or immunogenicity, determining the composition of the carbohydrates attached to a protein is important. Characterization of carbohydrates is required for biologics (therapeutic glycoproteins, vaccines, etc.) to show composition of matter and consistency of manufacture, resulting in a need for extensive characterization of product. Thus, the ability to remove some or all of the glycans from a protein and to analyze the carbohydrate or the protein, or both, to determine their composition or compositions is useful both for quality control and often for determining whether a protein will have a desired therapeutic efficacy or other effect.

For most analytical techniques, the glycans must be released or removed from the protein before analysis can be performed. Glycan removal, or "deglycosylation", is achieved by one of two methods, enzymatic digestion or chemical release. In enzymatic digestion, for example, N-glycans are released from glycoproteins by enzymatic cleavage with PNGase F (Peptide-N4-(acetyl-β-glucosaminyl)-asparagine amidase, EC 3.5.1.52) or other endoglycosidases such as endo-alpha-N-acetyl-galactosaminidase, Endoglycosidase F1, Endoglycosidase F2, Endoglycosidase F3, Endoglycosidase H, and the like, and are then treated to label their free-reducing terminus with a fluorescent dye for analysis by methods such as high performance liquid chromatography (HPLC), capillary electrophoresis (CE), carbohydrate gel electrophoresis, or mass spectrometry. In chemical release, the glycoprotein is typically subjected to hydrazinolysis or trifluoromethanesulfonic acid (TFMS). TFMS, for example, removes all N- and O-linked glycans. Unfortunately, it also destroys the carbohydrates, rendering it unsuitable for use in applications in which analysis of the carbohydrates is important. Both the enzymatic and the chemical deglycosylation procedures encompass multiple steps, extended incubation times, and clean-up steps prior to analysis of the released glycans.

Fluorescent labeling of glycans facilitates their sensitive detection as well as contributes to improved resolution. Released N-glycans are most commonly labeled by reductive amination, where the free-reducing end of a glycan is conjugated to the free amino group of a fluorescent dye. Fluorescent labeling of glycans by reductive amination usually requires anhydrous conditions, elevated temperatures and extended incubation times, which may result in a partial degradation of labile constituents of N-glycans, such as sialic acids.

Therefore, there is a need for more rapid methods that can be performed under relatively mild conditions, that reduce handling and clean up steps, that are suitable for use with multiple analytic methods, and that improve the amount and types of glycans released. Surprisingly, the present invention meets these and other needs.

BRIEF SUMMARY OF THE INVENTION

In a first group of embodiments, the invention provides methods of releasing glycans from a glycoprotein. This group of methods comprises the following steps, taken in the following order: step (a), in which the glycoprotein is contacted with a solution comprising a denaturing reagent, for a time sufficient to denature the glycoprotein; step (b), in which the glycoprotein is immobilized on a material that binds protein; and, step (c), in which the glycoprotein is incubated with an endoglycosidase at a temperature of 40° C. to 50° C. for 5 minutes to 3 hours, thereby releasing glycans from the protein. In some embodiments, the methods further comprise step (b'), in which the material that binds protein is contacted with a non-glycoprotein, non-detergent blocking agent, between step (b) and step (c). In some embodiments, the methods further comprise step (d), in which the released glycans are contacted with a weak acid. In some embodiments, the methods further comprise washing the glycoprotein with buffer between steps (a) and (b) and, optionally, between steps (b') and (c). In some embodiments, the incubating of the glycoprotein and the endoglycosidase is for 15 minutes to 1 hour. In some embodiments, the incubating of the glycoprotein and the endoglycosidase is at 44° C. to 46° C. In some embodiments, the endoglycosidase is PNGase F. In some embodiments, the weak acid is acetic acid. In some embodiments, the material that binds protein is nitrocellulose membrane. In some embodiments, steps (a) and (b) are conducted in a centrifugable device. In some embodiments, steps (a) and (b) are conducted in a well on a plate. In some embodiments, the denaturing reagent is a chaotrope. In some embodiments, the non-glycoprotein, non-detergent blocking agent is polyvinyl pyrrolidone.

In a second group of embodiments, the invention provides methods for releasing glycans from a glycoprotein, comprising incubating the glycoprotein with an endoglycosidase at a temperature of 40° C. to 50° C. for 5 minutes to 3 hours, thereby releasing the glycans from the protein. In some embodiments, the incubating of the glycoprotein and the endoglycosidase is for 15 minutes to 1 hour. In some embodiments, the incubating of the glycoprotein and the endoglycosidase is at 44° C. to 46° C. In some embodiments, the incubating of the glycoprotein and the endoglycosidase is at 44° C. to 46° C. and the incubation is conducted for 1 to 3 hours.

DETAILED DESCRIPTION OF THE INVENTION

Introduction

Removing carbohydrates from proteins, a process called "deglycosylation," is important for a variety of biotechnology processes. Analysis of the profile of the released carbohydrates is important, for example not only for proteins intended for therapeutic use, in which the carbohydrates placed on the protein may determine clinical efficacy, but also in production of recombinant proteins, in which a change in carbohydrate profile may indicate stress in the system, signaling conditions that may require a commercial-scale fermenter of expensive protein to be discarded.

A subset of proteins can be deglycosylated under native, or non-denaturing, conditions, in which the protein is simply mixed with an enzyme that will release from the protein the glycans conjugated to the protein. These methods have the advantage of mild conditions and simple clean up, but often result in incomplete release of glycans. Most proteins, however, need to be denatured before they can be deglycosylated. For example, the secondary and tertiary structures of these proteins may not permit access of the enzyme to the carbohydrates unless the protein is first denatured to alter those structures. Typical protocols for denaturing involve the use of detergents and reducing agents, and an overnight incubation. For example, these protocols typically adding to the glycoprotein a reducing agent such as beta-mercaptoethanol, an anionic detergent, such as sodium dodecyl (lauryl) sulfate, a non-ionic detergent, such as octylphenolpoly(ethyleneglycolether), and a deglycosylating enzyme, and incubating the resulting mixture for 16 hours at 37° C. Once the protein is deglycosylated, the glycans are removed and usually, are labeled. These protocols are effective and largely independent of the protein (that is, they can be used on most proteins), but are harsh, typically use detergents, which must be removed before some analytical processes can be conducted, and have more clean-up steps.

In commercial fermentation settings, the length of sample processing, typically at least a day, when these standard deglycosylation methods are used reduces the possibility of using carbohydrate analysis as a marker for rapid, in-process analysis and as a tool for control of process variables, such as stress during the fermentation process. The use of detergents adds steps and time since any detergent remaining with the released glycans can interfere with the results of mass spectrometry or other techniques used to analyze the carbohydrate profile.

Surprisingly, the methods of the present invention solve the problems discussed above by providing a method for releasing glycans from proteins in as little as an hour and having them ready for labeling in as little as two hours. If it is only necessary to have a representative glycan profile rather than a complete one, deglycosylation can be achieved in as little as 10-15 minutes. For example, for a process control assay to determine if conditions in a fermenter vat are producing the proper glycoprotein, deglycosylation with a much lower yield, but with a representative profile, may be all that is necessary to tell the operator that the fermentation conditions need adjustment. Thus, in these applications, the rapid deglycosylation afforded by the inventive methods makes available almost real time analysis and feedback of fermentation conditions.

Studies using the exemplar deglycosylation enzyme N-glycosidase F, or "PNGase F," an enzyme first isolated from *Flavobacterium meningosepticum*, showed, surprisingly, that for certain glycoproteins, such as fusion proteins, the methods of the invention released greater total glycan yields than did traditional protocols. Unexpectedly, the protocols of the invention also resulted in greater yields of certain glycan species that were not effectively released when the protein sample was deglycosylated following more traditional protocols. For example, in certain fusion or chimeric glycoproteins, the high mannose glycan known as MANS glycan (also known as (Man)5(GlcNAc)$_2$, mannopentaose-di-(N-acetyl-D-glucosamine), or oligomannose-5 glycan), may not be effectively released by PNGase F under a standard 16 hour incubation at 37° C., but are effectively released using rapid deglycosylation protocols disclosed herein. Thus, the protocols of the invention not only permit faster deglycosylation of glycoproteins, but surprisingly improve both the yield and species of glycans released. Without wishing to be bound by theory, it is believed that the methods of the invention permit the PNGase F enzyme to cleave glycan linkages that become more accessible or cleave more efficiently less preferred substrates for the enzyme, and therefore can provide for analysis a more representative set of glycans from a protein sample than can current, commonly used protocols. This is important, as the analysis of the glycans rests on how representative is the sample submitted for analysis.

The inventive methods afford a non-selective, quantitative release and recovery of intact glycans. In some embodiments, the glycans are N-glycans. In some embodiments, the glycans are O-glycans. As persons of skill are aware, a variety of deglycosylating enzymes are known, including PNGase F, PNGase A, endo-alpha-N-acetyl-galactosaminidase, Endoglycosidase F1, Endoglycosidase F2, Endoglycosidase F3, and Endoglycosidase H are known. Recombinant PNGase F, is commercially available from ProZyme Inc. (San Leandro, Calif.), while most of the other enzymes are commercially available from several sources, including ProZyme. These and other enzymes have utility depending on the expected glycan profile of the protein of interest or on the particular glycan whose presence needs to be detected. In some embodiments of the invention, one or more of these enzymes can be used in the methods of the invention as set forth below.

In our own protocols, we were using a combination of three reagents, including a reducing agent and a carboxymethylation reagent as part of the denaturing process. Against conventional wisdom, we discovered that better results could be obtained by eliminating all but the denaturation reagent and using the methods set forth in this disclosure. Thus, the inventive methods also avoid the use of detergents, reducing agents and carboxymethylation reagent. In particular, the inventive methods avoid the additional steps and time that would otherwise be needed to remove the detergents from the released glycans prior to analysis.

The mild conditions used for the denaturation prior to deglycosylation in the inventive methods also preserve labile carbohydrates, such as sialic acids. If desired, the protein sample can be recovered and analyzed for confirmation of deglycosylation. Deglycosylation of a recombinant protein, for example, is usually determined by determining by gel electrophoresis or mass spectrometry the molecular weight of the protein following the deglycosylation procedure and comparing it to the predicted weight of the amino acid residues.

Further, in some embodiments, the inventive methods use a protein-binding membrane in combination with centrifugation to perform the steps on the protein binding membrane in a way that simplifies the procedure, minimizes losses due to handling and reduces the possibility of contamination. The methods employing centrifugation also facilitate rapid exchange of reagents, and rapid separation of the glycans, once released from the glycoprotein, from the now-deglycosylated protein.

In sum, the methods of the invention not only provide faster and simpler processes for glycan removal and analysis, but with at least some more glycosylated and hard to analyze proteins, result in greater release of glycans and a more complete glycan profile than do more traditional protocols.

THE METHODS OF THE INVENTION

A. Denaturing

In their simplest form, the methods of the invention employ the following steps. First, the protein sample is denatured by contacting with a solution comprising a chaotropic salt (referred to as "Binding Buffer" in FIG. 1). A number of such chaotropic salts are known and can be used as a denaturing reagent in the methods of the invention. In some embodiments, for example, the chaotropic salt is a guanidinium salt such as guanidinium chloride, guanidinium thiocyanate, guanidinium hydrochloride or urea. In some preferred embodiments, the salt is guanidinium hydrochloride. In some embodiments, a combination of chaotropic salts may be used. For convenience of reference, the chaotropic salt or salts will be referred to individually or collectively as a "chaotrope."

The chaotrope is used at a concentration of 3-8 molar; in some embodiments, the chaotrope is at a concentration of 3-7 molar, in some embodiments, the chaotrope is at a concentration of 4-6 molar, or 5-6.5 molar, with 6 molar being preferred. The ratio of glycoprotein sample to chaotrope should be a minimum of 1:1, but it is not particularly important if the ratio of glycoprotein to the chaotrope is higher, with 1:10, 1:50, or 1:100 or more being acceptable, though unnecessary. The denaturation occurs quickly, so the time of incubation is not particularly critical, with 1 minute to 15 minutes being typical. In some embodiments, the incubation is 3-7 minutes, in some embodiments, the incubation is 5 minutes.

In some embodiments, other denaturing reagents, such as detergents and reducing agents known in the art, can be used. These embodiments, however will generally require additional step to remove the detergent and the like. Further, the use of a chaotrope permits more complete deglycosylation of proteins that are normally insoluble in aqueous solutions. Thus, use of a chaotrope as the denaturing reagent is preferred as the chaotrope is capable of denaturing a broader class of proteins.

B. Immobilization on a Protein Binding Surface

The protein sample is then immobilized on a surface that binds proteins. A number of such surfaces are known in the art and can be used to bind proteins in the methods of the invention. In some embodiments, the surface used to immobilize the protein sample is nitrocellulose membrane, which is widely used for binding proteins and readily available commercially from, for example, Invitrogen Corp., (Carlsbad, Calif.). In some embodiments, the surface used to immobilize the protein sample is polyvinylidene fluoride, or "PVDF". PVDF is commercially available from a number of sources, including Millipore Corp. (Billerica, Mass.) and Boedeker Plastics, Inc. (Shiner, Tex.). In some embodiments, the surface used to immobilize the protein sample is nylon, which is of course also widely commercially available. For convenience, the discussion below will refer to the material used to immobilize the protein sample (such as nitrocellulose membrane, PVDF, or nylon) as the "protein binding material." Whatever the material used, in some of the methods, it preferably has pores, which provides advantages discussed further below.

We have noted one prior method for denaturing protein that used immobilization on nitrocellulose membrane, but in that protocol, the protein was first immobilized and then denatured. We have found that the sequence of steps makes a difference, and that denaturing first, and then immobilizing results in the recovery of some 20-30% more glycan than the previous technique of immobilization followed by denaturation. Thus, altering the order of these two steps alone substantially improves the result of the deglycosylation procedure.

C. Wells and Centrifugable Devices

In some embodiments, the protein binding material is positioned on a surface. Conveniently, the protein binding material is positioned at the bottom of a well of a 6-, 8-12-, 24-, 48- or 96-well cell culture plate or microtiter plate. In such embodiments, the denaturing reagent, such as a chaotrope, may be removed by suctioning. In some embodiments, the protein binding material is disposed in a device adapted for use in a centrifuge so that the separation of reagents from the protein sample can be assisted by centrifugal force. A number of such devices, which for convenience may be referred to as "centrifugable devices," are available commercially and may include not only traditional centrifuge tubes, but also for example vials, cylinders, plates and strips. In some embodiments, the centrifugable device is a centrifuge tube. In some embodiments, the centrifugable device is a vial. In some embodiments, the centrifugable device is a plate. In some embodiments, the centrifugable device is a cylinder. In some embodiments, the centrifugable device is a strip. The particular centrifugable device is generally not critical so long as it can contain the reagent, and can be centrifuged to permit centrifugal force to assist steps in which the reagents, such as wash buffers and the enzyme(s) used as the deglycosylation reagent, are separated from the glycoprotein immobilized on the protein binding material.

In preferred embodiments, the centrifugable device is configured to permit the protein binding material to be positioned sufficiently above the bottom of the tube to leave a space for reagents to drain into when they are separated from the glycoprotein sample by centrifugal force. Preferably, the protein binding material has pores small enough to prevent the solution containing the chaotrope or other reagents from seeping through in the absence of centrifugation, but large enough to permit the reagent solution to flow through the material into the tube when the tube (and the protein binding material disposed within it) is subjected to centrifugation. When the protein sample and chaotrope are placed on the protein binding agent, the chaotrope can then conveniently be separated and removed from the protein sample by a brief centrifugation, which forces the solution comprising the chaotrope through the pores of the membrane and into the bottom of the tube. Preferably, the centrifuge tube is selected so that the volume available below the point at which the protein binding material is positioned is larger than the volume of reagents to be used.

In some embodiments, the centrifugable device can be configured with an internal circumferential ring or a horizontal surface with holes disposed above the bottom of the tube to hold the protein binding material above the bottom of the tube. In some embodiments, the centrifuge tube has a removable internal component that can hold the nitrocellulose membrane or other protein binding material and carry it to another tube when desired. Such tubes and such removable inserts are commercially available. For example, Millipore Corp. (Billerica, Mass.) sells tubes with removable inserts suitable for use in the invention, such as the Micropure®-EZ enzyme remover, complete with a membrane that binds proteins. The Micropure®-EZ tubes are convenient for use in capturing denatured glycoprotein and performing other steps in the deglycosylation protocols of the invention. Millipore also sells filter inserts that fit standard 0.5 mL microcentrifuge tubes. These inserts can conveniently be used as a platform on which to place the protein binding material in the methods of the present invention and to transport the protein binding material to, for example, a fresh standard 0.5 microcentrifuge tube when desired. For clarity, it is noted that the step of contacting the glycoprotein with the chaotrope-containing solution and the step of contacting the glycoprotein (now denatured) with the protein binding material can be performed in any convenient container, and the protein sample then contacted with the protein binding material in the centrifuge tube.

Centrifugation is a laboratory technique well known to persons of skill. Thus, while for convenience the discussion below will be drawn particularly to the use of the Millipore microcentrifuge tubes described above, it is expected that persons of skill can readily adapt the protocol to the use of different or larger tubes and centrifuges if desired.

Whichever means of holding the protein binding material is used, once the protein sample is denatured by the chaotrope, placement of the protein binding agent in the centrifuge tube permits the chaotrope to be removed from the sample simply by centrifuging the tube. The equivalent of a short high speed microcentrifugation is satisfactory. For use with the Millipore tubes described above, for example, a 2 minute centrifugation at 14,000 rpm gives satisfactory results.

D. Blocking

Figure 1:
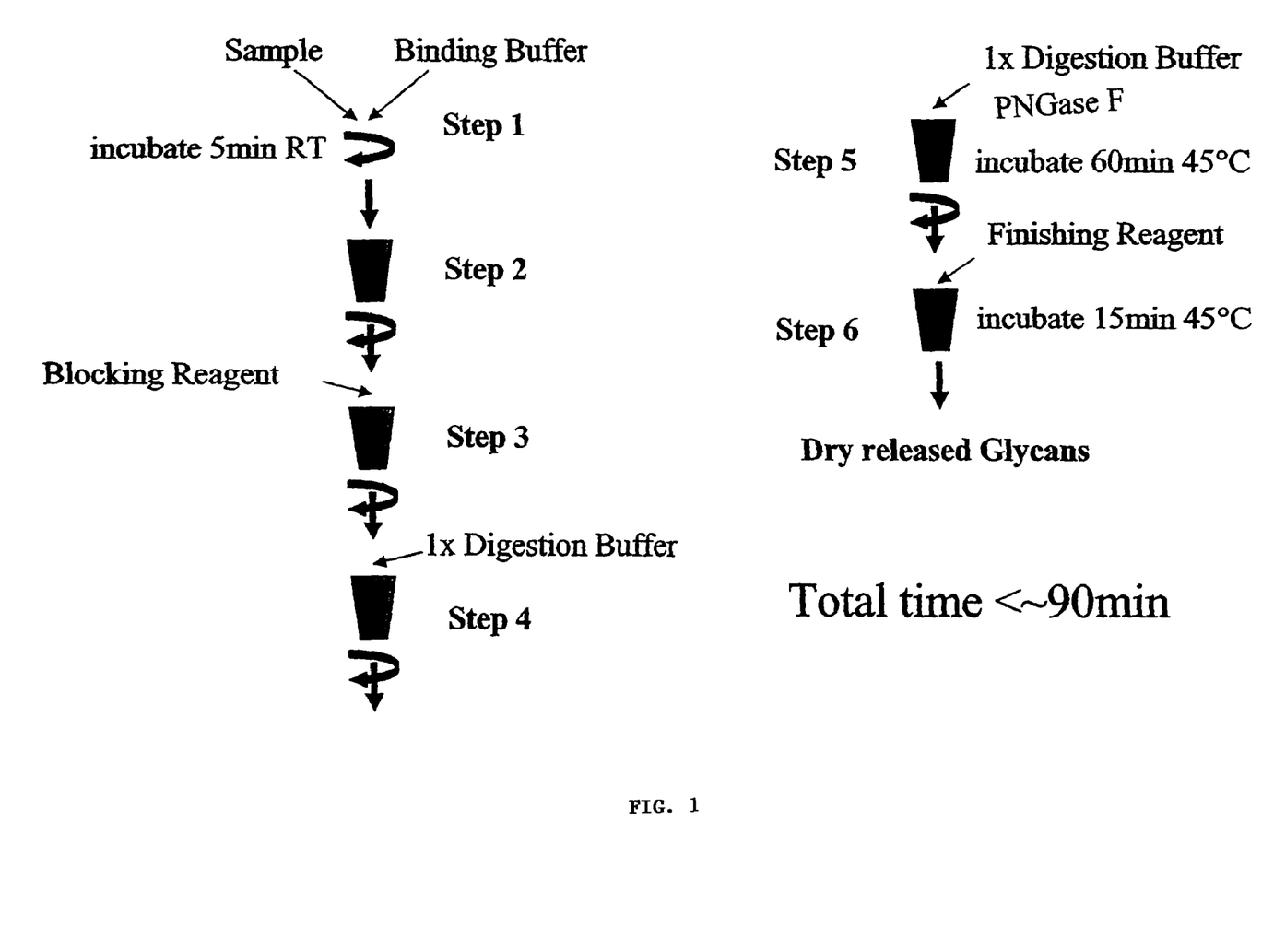
FIG. 1 is a flow diagram showing an embodiment of the methods of the invention. RT: room temperature. Curved arrows represent centrifugation of the mixture between steps.

If the amount of the protein sample available for analysis is substantial, and will completely cover the protein binding material, there is no need to add a blocking agent (referred to as "Blocking Reagent" in FIG. 1). If the amount of protein available is modest, however, or simply as a precaution, a blocking agent may be used so that the enzyme is not trapped on any of the protein binding material that is not covered by the protein sample and is therefore unavailable to release glycans from the protein sample. The concentration of the agent is not critical so long as there is enough for non-specific binding to the protein binding material. Typically, a 1-5% solution is sufficient. Use of blocking agents is well known in the art, and it is expected that the person of skill is generally familiar with their use.

A number of blocking agents are known in the art and can be used so long as they are not a glycoprotein or a detergent. For example, in some embodiments, the blocking agent is bovine serum albumin, while in others it is polyvinyl pyrrolidone. If the protein binding material is placed on a solid surface, such as the bottom of a well on a plate, and the reagents are removed by suctioning them off, the size of the polyvinyl pyrrolidone is not material. For use in methods of the invention involving membranes with pores, and centrifugation, discussed below, if polyvinyl pyrrolidone is used as the blocking agent, it is preferable that the polyvinyl pyrrolidone is of a size that can pass through the pores. In such uses, for example, the polyvinyl pyrrolidone is preferably 5-50 kD, with 5-25 kD polyvinyl pyrrolidone being used in some embodiments, 5-15 kD polyvinyl pyrrolidone being used in some other embodiments, and 10 kD polyvinyl pyrrolidone being preferred. It will be understood that the blocking buffer and other reagents discussed herein will generally not pass through the membrane due to surface tension, but that it is desirable that the liquid reagents be able to pass through the pores of the membrane under centrifugation (it is understood that the protein sample will not release from the protein binding agent under the centrifugation steps discussed). Whether any particular size of polyvinyl pyrrolidone can pass through pores of any particular membrane of choice for use in the invention can be determined by simply suspending the membrane midway in a centrifuge tube, placing a bead of the polyvinyl pyrrolidone on the membrane, centrifuging the tube for the time and at the speed contemplated for use in the method, and seeing if the polyvinyl pyrrolidone has passed through the membrane. If it has, it is of a suitable size.

E. Washing

The protein sample is then washed once with a buffer (referred to as "Digestion Buffer" in FIG. 1). Deglycosylation enzymes have been used in the art for some years, and a large literature exists. The buffer can be any standard laboratory buffer that the literature indicates is compatible with the deglycosylation enzyme to be used. For use with the exemplar enzyme PNGase F, for example, in some embodiments, the buffer is tris hydrochloride, in others, phosphate buffered saline, in others, it is ammonium bicarbonate, and in still others, it is ammonium formate. The concentration of the buffer is typically 5 to 100 millimolar, in some embodiments, 5 to 50 millimolar, in others 5 to 25 millimolar, in others 5-15 millimolar, and in others 5-10 millimolar, while in yet others, it is 5 millimolar.

The wash is generally performed to reduce the chance that there is a carryover of some of the chaotrope in, for example, voids that may exist between protein binding material and the well, or between inner and outer tubes of the centrifuge tube. If the protein sample is immobilized in a well, the wash buffer is suctioned off, while in the centrifuge tube embodiments, the tube is given a short spin to force the wash through the pores. For example, spinning the tube for 2 minutes at 10000 rpm is satisfactory.

F. Temperature, Time, and Release of Glycans

The protein sample is now ready for release of the glycans. If the method is being performed in a centrifuge tube, the protein binding material, with the bound protein sample, is now moved to a fresh centrifuge tube so that the glycans will not be released into the buffer and reagents that will have accumulated at the bottom of the original tube. The deglycosylation enzyme, such as PNGase F, typically in the buffer used in the wash step above, is then added to the protein sample and gently shaken or vortexed to thoroughly contact the protein sample with the enzyme. Concentrations of enzymes for use in deglycosylation are well known to persons of skill. With respect to PNGase F, for example, a suitable final concentration upon dilution is 0.5 Unit/mL. In methods using centrifugable devices, such as tubes, the solution comprising the enzyme will remain in contact with the protein sample on the membrane due to surface tension until later the device (such as a tube) is centrifuged to create sufficient force to cause the enzyme-containing solution through the pores of the membrane.

Figure 2:
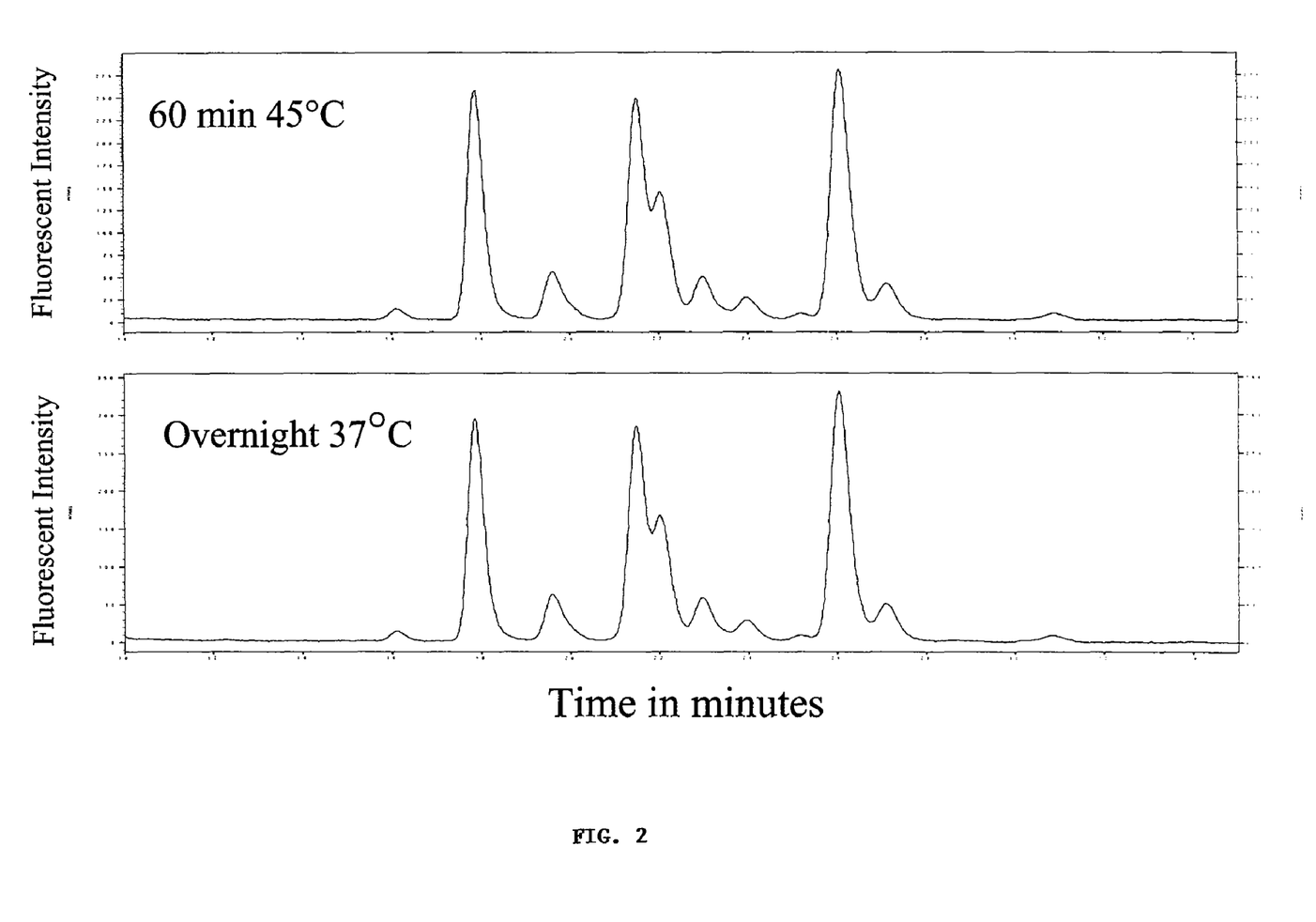
FIG. 2 presents printouts of high pressure liquid chromatography (HPLC) elution profiles of glycans released from desialylated, human polyclonal antibody by (top printout) a 60 minute incubation of the antibodies with PNGase F at 45° C. and (bottom printout) overnight incubation of the antibodies with PNGase F at 37° C. Both printouts: Y axis: Fluorescence intensity. X axis: Time at which the glycan eluted from the HPLC column, in minutes.
Figure 3:
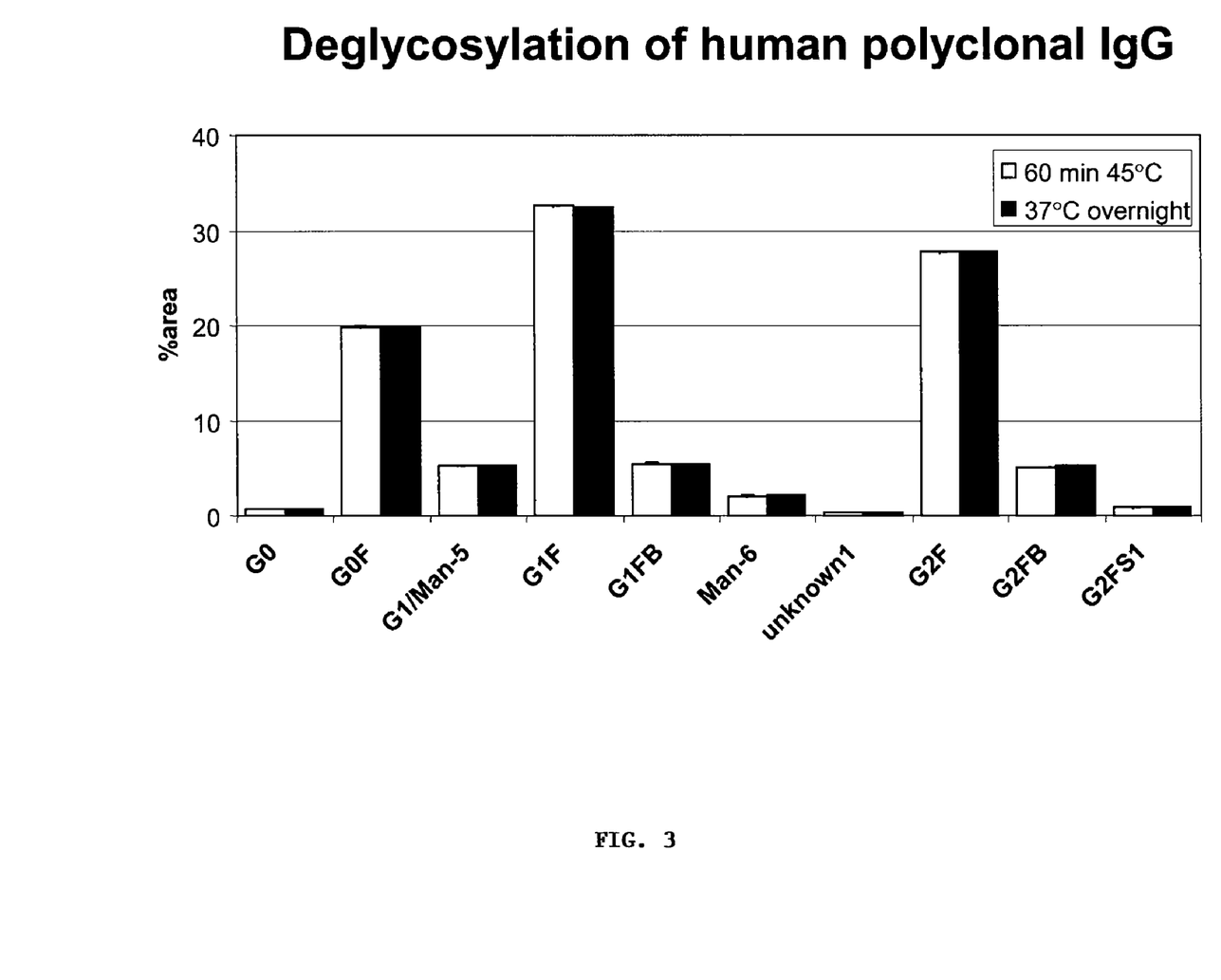
FIG. 3 is a graphical depiction of the data presented in FIGS. 2A and B. Each of the various glycans released from the antibodies is labeled along the X axis. The Y axis is labeled "% area", representing the area under the peak of the HPLC elution curve for the glycan. This figure correlates with the mole percent of each glycan.
Figure 4:
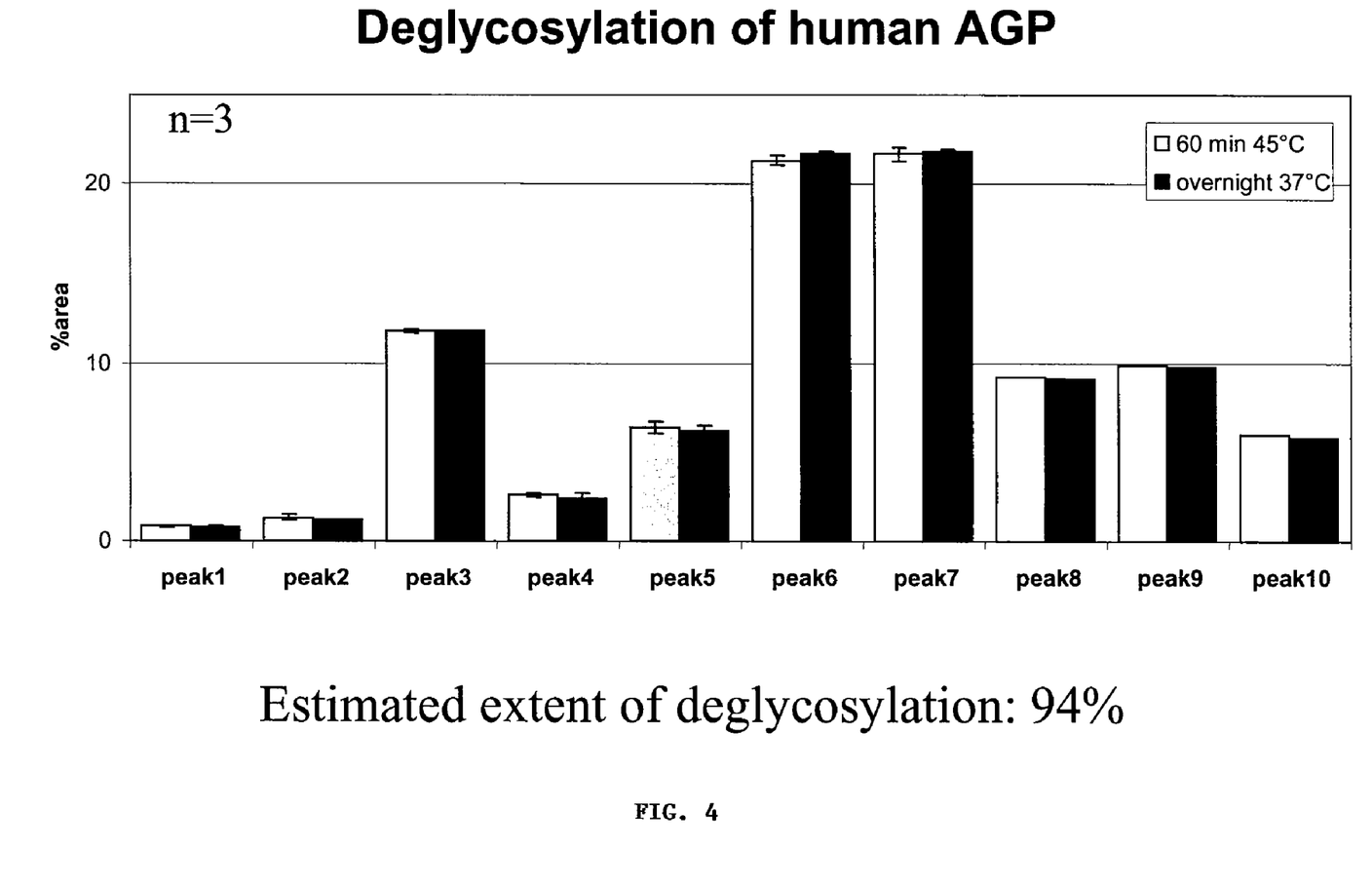
FIG. 4 is a graphical depiction of the release of glycans from the human glycoprotein α-1-acid glycoprotein, or "AGP", AGP, also known as orosomucoid, is a blood glycoprotein produced in the liver that is highly glycosylated, with a high sialic acid content. It is often used in the art to show release of certain glycans. Each of the various glycans released from the AGP is labeled along the X axis. The Y axis is labeled "% area", representing the area under the peak of the HPLC elution curve for the glycan.

For over 20 years, the standard incubation methods for deglycosylation of glycoproteins have included incubation of the protein sample with the deglycosylation enzyme for 16 hours, or more, at 37° C. Surprisingly, we have found that glycan release comparable to that achieved by the standard protocols can be achieved by dramatically shortening the time of incubation, but modestly increasing the temperature. FIGS. 2-4 set forth the amount and type of glycans released from human polyclonal antibodies (FIGS. 2 and 3) and from human α-1-acid glycoprotein (FIG. 4), a highly glycosylated glycoprotein containing a number of sialic acids. As shown in the Figures, the amount and types of glycans released after incubation of the glycoproteins with the exemplar deglycosylation enzyme PNGase F for 1 hour at 45° C. are almost indistinguishable from the profile of glycans released from the glycoproteins after 16 hour incubation ("overnight") with the same enzyme at 37° C. Studies of the two methods using a number of other glycoproteins, including a monoclonal antibody, RNAse B, ovalbumin, human transferrin, bovine fetuin, and a fusion protein. For each glycoprotein, the elution profiles of the glycans by HPLC for the two methods were close to or almost indistinguishable from one another. While it might have been expected that a relatively modest increase in temperature would reduce the incubation time required by a modest amount, the dramatic reduction in incubation time to obtain virtually identical results was a surprising result. Raising the temperature of the incubation therefore is surprisingly advantageous.

Persons of skill will recognize that there is an inverse relationship between temperature and enzyme activity, but also a point at which enzyme activity will diminish or even disappear. Studies of glycan release from glycoprotein in solution (and therefore not in combination with the protein immobilization steps discussed above) showed, for example, that the amount of glycan released in a one hour incubation with PNGase F at 55° C. was only a quarter as much as was released in a one hour incubation at 50° C., while the amount released at 45° C. was substantially higher than the amounts released at either 37° C. or at 50° C. From these studies, we expect that incubation with a deglycosylation enzyme at temperatures from 40-50° C. will result in useful release of glycans. At 44-46° C., in some embodiments, the incubation is from 30 minutes to 4 hours, while conveniently in some embodiments, it is from 45 minutes to 3 hours. In other embodiments, the incubation is from 1 hour to 2 hours and in other embodiments, is about 1 hour (with regard to the times stated herein, "about" means plus or minus 5 minutes). With temperatures between 40-44° C., longer incubation times will generally be useful, with the time increasing as the temperature of the incubation is lower; thus, in some embodiments, the incubation time is from 45 minutes to 4 hours, while in others it is from 1 hour minutes to 3 hours, in some embodiments is from 1 and a half hours to 3 hours and in other embodiments, is about 2 hours. Conversely, with temperatures between 46-50° C., shorter incubation times will generally be used, with the time decreasing as the temperature of the incubation is higher; thus, in some embodiments, the incubation time is from 5 minutes to 2 hours, while in others it is from 15 minutes to 1 and one half hours, in some embodiments is from 15 minutes to about 1 hour and at 49 or 50° C., is between 5 and about 45 minutes. Any particular time and temperature combination can be readily tested for its suitability with any particular glycoprotein of interest and deglycosylation enzyme by any of a number of assays, including aliquoting equal amounts of a solution containing the glycoprotein into tubes, incubating the aliquots with the deglycosylation enzyme at the time for the time and at the temperature of interest and comparing the total amount of glycans released to the amount released by incubation with the same enzyme at 37° C.

G. Collection of Glycans for Analysis

The sample holder is then allowed to cool back to room temperature for ease of handling. If the sample is in a centrifuge tube, the tube is then centrifuged, for example, 1 minute at 14,000 rpm to collect fluid containing the released glycans at the bottom of the tube (now referred to as the glycan sample), and the protein binding material and protein sample are removed to facilitate access to the glycans. If the sample holder is, for example, a well of a plate, the fluid in the well, now containing the released glycans, can be removed for analysis by any convenient means, such as pipetting, suctioning into a fresh container, decanting, or the like.

H. Formation of a Free Reducing Terminus for Labeling of Glycans

Optionally, to facilitate labeling of the glycans, a weak acid is added (referred to as "Finishing Reagent" in FIG. 1) to the glycan sample to convert the glycans to a form with a free reducing terminus. This permits adding a fluorescent label by reductive amination chemistry well known in the art. Conversely, if glycan analysis will use a procedure other than fluorescent labeling (for example, if the analysis will be by mass spectrometry) or fluorescent labeling by other means than reductive amination, the finishing reagent is not needed.

Since removing the acid by evaporating avoids additional steps and additional reagent, preferably, the acid is preferably a volatile acid, such as hydrochloric acid or acetic acid, rather than one, like sulphuric acid, that is not. Acetic acid is particularly preferred for ease of handling. Some glycans, such as sialic acid, are sensitive to heat and acidic conditions. Thus, the concentration of acid to be added is preferably 1 M or less and in some embodiments, is 500 millimolar or less, while in others it is 400 millimolar or less, in others it is 300 millimolar or less, in others it is 250 millimolar or less, in others it is 200 millimolar or less, in others it is 150 millimolar or less, and in others it is 100 millimolar or less. For example, in some embodiments, the addition of acid is of 5 microliters of 100 millimolar acetic acid per 50 microliters of glycan. The finishing reagent and the glycan sample are shaken or gently vortexed and briefly incubated, for 5 to 30 minutes at 40-47° C., in some embodiments for 10-25 minutes at 40-47° C., in some embodiments for 12-20 minutes at 40-47° C., in some embodiments for about 15 minutes at 40-47° C., with "about" meaning plus or minus one minute. In some embodiments, the incubation is at 41-47° C., in some it is at 42-47° C., in some it is at 43-46° C., and in some it is at 44.5-45.5° C. The glycan sample can then be labeled by any conventional means.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of releasing glycans from a glycoprotein, consisting essentially of, in the following order,
   (a) contacting said glycoprotein with a solution comprising a denaturing reagent, for a time sufficient to denature said glycoprotein;
   (b) immobilizing said glycoprotein on a material that binds protein; and,
   (c) incubating said immobilized glycoprotein with a deglycosylation enzyme, thereby releasing said glycans from said glycoprotein.

2. The method of claim 1, further comprising step (b'), contacting said material that binds protein with a non-glycoprotein, non-detergent blocking agent, between step (b) and step (c).

3. The method of claim 2, further comprising washing said glycoprotein with buffer between steps (b') and (c).

4. The method of claim 2, wherein said non-glycoprotein, non-detergent blocking agent is polyvinyl pyrrolidone.

5. The method of claim 1, further comprising washing said glycoprotein with buffer between steps (b) and (c).

6. The method of claim 1, further comprising step (d) contacting said released glycans with a weak acid.

7. The method of claim 6, wherein said weak acid is acetic acid.

8. The method of claim 1, wherein said incubating of said glycoprotein and said deglycosylation enzyme is for 15 minutes to about 1 hour.

9. The method of claim 1, wherein said deglycosylation enzyme is PNGase F.

10. The method of claim 1, wherein said material that binds protein is nitrocellulose membrane.

11. The method of claim 1, wherein said steps (a) and (b) are conducted in a centrifugable device.

12. The method of claim 1, wherein said steps (a) and (b) are conducted in a well on a plate.

13. The method of claim 1, wherein said denaturing reagent is a chaotrope.

14. The method of claim 1, wherein the glycoprotein is an antibody or monoclonal antibody.

15. The method of claim 1, wherein the glycoprotein is a fusion protein.

16. The method of claim 1, wherein said incubating of said glycoprotein and said deglycosylation enzyme is conducted in the absence of a detergent.

17. The method of claim 1, wherein said incubating of said glycoprotein and said deglycosylation enzyme is conducted in the absence of a reducing agent and a carboxymethylation reagent.

* * * * *